United States Patent
Dieckmann et al.

[11] Patent Number: 6,003,362
[45] Date of Patent: *Dec. 21, 1999

[54] APPARATUS FOR MEASURING THE PARTIAL PRESSURE OF GASES DISSOLVED IN LIQUIDS

[75] Inventors: Michael Dieckmann; Rainer Buchholz, both of Berlin, Germany

[73] Assignee: Euroferm GmbH i.G., Berlin, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/878,920

[22] Filed: Jun. 19, 1997

Related U.S. Application Data

[63] Continuation-in-part of application No. 08/561,910, Nov. 22, 1995, abandoned.

[30] Foreign Application Priority Data

Dec. 21, 1994 [DE] Germany ............... 44 45 668
Jun. 21, 1996 [DE] Germany ............. 196 24 844

[51] Int. Cl.$^6$ .................. G01N 21/55; G01N 21/85; G01N 21/61
[52] U.S. Cl. .................. 73/19.12; 73/19.05; 356/43
[58] Field of Search ................ 73/19.12, 19.05; 250/343, 339.12; 356/437, 432; 422/91

[56] References Cited

U.S. PATENT DOCUMENTS

| | | |
|---|---|---|
| 4,041,932 | 8/1977 | Fostick . |
| 4,201,222 | 5/1980 | Haase . |
| 4,550,590 | 11/1985 | Kesson .................. 73/19.05 |
| 4,892,383 | 1/1990 | Klainer et al. ............. 385/12 |
| 5,116,759 | 5/1992 | Klainer et al. ........... 435/287.2 |
| 5,144,831 | 9/1992 | Hale et al. ............... 73/19.05 |

FOREIGN PATENT DOCUMENTS

| | | |
|---|---|---|
| 0253559 | 1/1988 | European Pat. Off. . |
| 3344019 | 6/1985 | Germany . |
| 4028354 | 3/1991 | Germany . |
| 4418180 | 1/1996 | Germany . |
| 4445668 | 6/1996 | Germany . |

OTHER PUBLICATIONS

"Putting The Right Fizz in Beer", The Chemical Engineer, No. 498, 1991.

J. Buerck et al, "Fiber–Optic Evanescent Wave Sensor for in Situ Determination of Non–Polar Organic Compounds in Water", Sensors and Actuators B, BD. B18, No. 1/03, Mar. 1, 1994, pp. 291–295.

V. Ruddy et al, "Detection of Propane by IR–ATR in a Teflon (R)–Clad Fluoride Glass Optical Fiber" Applied Spectroscopy, BD. 44, No. 9, Nov. 1, 1990, pp. 1462–1463.

Ertan–Lamontagne M C et al, "Polymer–Coated, Tapered Cylindrical ATR Elements for Sensitive Detection of Organic Solutes in Water" Applied Spectroscopy, BD. 49, No. 8, Aug. 1, 1995, pp. 1170–1173.

Fresenius J. Anal. Chem (1992) 243: 42–46: Fabrication and characterization of a sterilizable pH–optrode by Jianzhong Zhu, Yunlong Jin and Jinagqi Xue.

(List continued on next page.)

*Primary Examiner*—Hezron Williams
*Assistant Examiner*—Jay L. Politzer
*Attorney, Agent, or Firm*—Friedrich Kueffner

[57] ABSTRACT

An method and an apparatus for measuring the partial pressure of gases dissolved in liquids in plants for carrying out biotechnological and food technological processes includes a measuring space which is separated by a gas-permeable diaphragm which is permeable for the gas to be determined. A light emission source produces a light ray with a wavelength which is absorbed by the gas to be determined. The light ray is directed into the measuring space. A measuring device is provided for determining the light ray leaving the measuring space. The measuring space, the light emission and the measuring device are arranged in a rod-shaped probe. The probe is capable of being sterilized. The measuring space is filled with a fluid which does not chemically react with the gas to be determined.

18 Claims, 2 Drawing Sheets

OTHER PUBLICATIONS

"Messmethoden zur Bestimmung jasföminger Luftverunreiningungen", G. Hermann Technology 498 (1991).

Frensenius J. Anal. Chem (1986) 325:387–392: Analytical chemistry with optical sensors by Otto S. Wolfbeis.

The Chemical Engineer, Technology, p. 18, 1991.

SPIE vol. 1012 In–Process Optical Measurements (1988), Aspects of Optical Fibers and Spectrometric in Chemical Process and Industrial Environments by Boisdé and Perez, pp. 58–65.

GIT Fachz. Lab. Jan. 1992, Faseroptischer ATR–Spektroskopie–Sensor, p. 37.

Rev. Sci. Instrum. 66 (4), Apr. 1995, 1995 American Institute of Physics Fibreoptic evanescent wave infrared spectroscopy of gases in liquids, D. Bunimovich, E. Belotserkovsky and A. Katzir, published Dec. 11, 1994.

Vibrational Spectroscopy 8 (1995) 103–108, Infrared fiber optic gas sensor for chlorofluorohydrocarbons, Mizaikoff, K. Taga, R. Kellner, Jun. 3, 1994.

Fresenius J. Anal. Chem (1994) 556–559, Fiber optic evanescent field sensors for gaseous species using MIR transparent fibers, K. Taga, B. Mizaikoff, R. Kellner, Aug. 9, 1993.

APPARATUS FOR MEASURING THE PARTIAL PRESSURE OF GASES DISSOLVED IN LIQUIDS

CROSS-REFERENCE TO RELATED APPLICATIONS

The present application is a continuation-in-part application of U.S. patent application Ser. No. 08/561,910 filed Nov. 22, 1995, abandoned.

BACKGROUND OF THE INVENTION

1. Field of the Invention

The present invention relates to an apparatus for measuring the partial gas pressure in liquid media.

2. Description of the Related Art

Primarily in the field of fermentation technology, it has increasingly been found necessary to carry out the measurement of gases through the determination of the partial pressure. For example, special probes have been developed for the determination of the partial oxygen pressure and the partial carbon dioxide pressure. A widely used example of these probes are the so-called Severinghaus electrodes. These devices operate with diaphragm-covered single-rod pH-electrodes. (DE-OS 25 08 637, Biotechnol. Bioeng. 22(1980), 2411–2416, Biotechnol. Bioeng. 23(1981), 461–466). In this system, an electrolyte solution or an electrolyte paste is located between the gas-selective diaphragm and the pH-electrode. The measuring principle is based on the fact that in an aqueous solution carbon dioxide forms carbonic acid which dissociates into a bicarbonate anion and a proton. This process results in the electrolyte solution in a pH-value change which is measured by means of the pH-probe. The disadvantage of this measuring principle is the fact that carbon dioxide is not measured directly, but in its ionic form. Since the portion of the ionic form is below 0.1%, this method is not sufficiently accurate. In addition, other volatile acid or basic gases impair the pH-value measurement. Also, the maintenance costs are very high.

Also known from the prior art are $pCO_2$-optodes. These optodes also include a diaphragm-covered sensor system (SPIE Vol.798 Fiber Optic Sensors II (1987) p. 249/252; Anal. Chim. Acta 160 (1984) p. 305–309; Proc. Int. Meeting on Chemical Sensors, Fukuoka, Japan, Elsevier, p. 609–619, (1983), Talanta 35(1988)2 p. 109–112. Anal. Chem. 65(1993) p.331–337, Fresenius Z. Anal. Chem. 325(1986) p.387–392). The pH-optodes use as indicator phase pH-indicators which change their absorption properties or fluorescence properties in dependence on the proton concentration (Anal. Chem. 52(1980) S. 864–869, DE-OS 3 343 636 and 3 343 637. U.S. Pat. No. 855,364). When the indicator is separated from the substance being measured by means of a gas-permeable diaphragm, only gases, for example, carbon dioxide, can pass through the diaphragm to the indicator phase and can produce in the indicator phase a pH-value change by hydrolysis. The operation of such carbon dioxide optodes is analogous to the Severinghaus electrodes. The disadvantages of optical pH-measurements and, thus, $pCO_2$-measurements, are the very limited analytic measuring range and the dependency on ionic strength. The disadvantages already mentioned in connection with the Severinghaus electrodes also prevent the wide use of the optodes.

A differential pressure gage for the determination of carbonic acid is known from German Offenlegungsschrift 2 435 493. However, this device can only be used in flowing media. Accordingly, the device is particularly not suitable for use in conventional stirring or stationary reactors, as they are used particularly in the fermentation industry.

German Offenlegungsschrift 2 926 138 discloses a device for the continuous measurement for the content of dissolved carbon dioxide in liquids. The measuring principle is based on the determination of the conductivity differential. The device is equipped with a diaphragm, wherein liquid containing dissolved carbon dioxide flows against one side of the diaphragm and a neutral or basic measuring liquid flows against the other side of the diaphragm. A conductivity transducer each is arranged in the flow path of the measuring liquid in front of and following the permeable diaphragm. This measurement has the disadvantage that it is not suitable for liquids which change their chemical and physical properties.

In addition, it is known from European patent application 0 462 755 to determine gases, such as $CO_2$, by infrared absorption measurement. In this measurement, a ray of infrared light is conducted through the fluid to be measured. The light ray is divided into two or more components. These divided light rays are then measured. This measuring arrangement has the disadvantage that is does not permit the measurement of partial pressures and that it is sensitive to dispersive particles of the sample liquid.

The division into two ray paths is already known from GB 2 194 333. In this method, only one light ray is conducted through the substance to be measured. The remaining radiation is used as reference light in order to increase the accuracy.

Also known in the art is a so-called chopped gas analysis device which also operates with luminescence diodes (Laser und Optoelektronik 17(1985)3, p. 308–310, Wiegleb, G.: Einsatz von LED-Strahlungsquellen in Analysengeräten [Use of LED-radiation sources in analysis devices]).

The known devices and methods have in common that they only measure concentrations. The substance to be measured is placed directly and measured in the path of radiation. This is possible for gases and liquids without dispersive particles with media-constant compositions in which disturbances can be taken into consideration by a blank value. However, the above-described optical methods are not capable of determining partial pressures. Also not possible is a use for liquids having compositions which change with the media and which contain particles which render the liquid turbid.

U.S. Pat. No. 5,116,759 discloses a measuring probe in which a measuring volume is defined by a diaphragm. Substances to be detected can diffuse through the diaphragm into the measuring volume where they react chemically with a sensing reagent. Thus, for example, a $CO_2$ measurement is based on a change of the pH value. The change of the reagent is then determined by measuring. This system has the disadvantage that the chemical sensing reagent is required. The sensing reagent and the diffusion process lead to a relatively long response time to the changes of the partial pressure in the sample space, wherein the response time may be in the order of magnitude of seconds to minutes because of the required diffusion into the measuring chamber. Another problem is the use in the case of very high partial pressures, because in that case too much light is absorbed and the measuring signal is too weak as a result.

Also known and described in the art is the analytic method of attenuated total reflectants (ATR). The measurement utilizes the phenomenon of the formation of evanescent waves or surface waves at the border surface between two optically differently dense media. In a medium having a high refraction number, a light ray is reflected back into the optically denser medium at the border surface to an optically thinner medium if the angle between the incident light ray and the perpendicular to the border surface exceeds the border angle of the total reflection. However, a portion of the light rays penetrate into the surrounding thinner medium by a few wave lengths and are only there reflected back into the optically denser medium. If light-absorbing substances are present in the area of this short light path, the reflected portion of the light becomes smaller. This weakening can be detected and correlated to the quantity of the absorbed substance.

A number of embodiments of the method for utilizing this light absorption phenomena are known in the art. Most ATR devices contain crystals, usually trapezoidally cut prisms. In DE-OS 42 27 813, very simple geometric shapes are described for the ATR element. Commercially available plane-convex microlenses of glass or of synthetic material, having the shape of hemispheres, are used.

In DE-OS 44 18 180, a cube corner reflector in the form of a triple prism is used. The advantage of this arrangement is its compact construction. The emitted light is deflected by 18°. This makes it possible to use the arrangement in a thin rod. Light wave conductors are used for supplying the light to be introduced and for removing the residual light.

DE-OS 40 38 354 discloses an ATR probe which does not use any prisms, lenses or similar components. The light is also conveyed through light conductors. The light conductors for supplying and removing light and the actual ATR sensor are composed of a common light conducting fiber, wherein the casing of the light conductor is removed in the area of the probe which does participate in the reaction. The light wave conductor is mechanically supported and is arranged in a probe body within a measuring chamber, so that the light wave conductor is in contact with the medium to be examined.

It is also known in the art to determine the $CO_2$ concentration in liquids by means of weakened total reflection (The Chemical Engineer 498 (1991) page 18). In a flow measuring cell for fluid substances, for example, beer, an attenuated total reflectance crystal (sapphire-ART) is arranged perpendicularly of the flow direction. The infrared light which is supplied at one side to the crystal travels through the crystal and is totally reflected several times. Each reflection causes the radiation to penetrate into the sample liquid by several $\mu$m and is weakened by the carbondioxide present in the substance The residual light liquids or gases can be used in the same manner. The type of the fluids depends on the gases to be measured.

In accordance with another preferred feature of the present invention, luminescent diodes are used as the light emission source. The use of these devices has the following advantages:

The emission has a relatively narrow band width, i.e., the use of interference filters is not absolutely necessary for selectively determining the respective gas. Because of the relatively low current consumption, it is possible in principle to construct the measuring arrangement with battery operation. A decisive advantage as compared to conventional infrared sources is the high constancy of power. Therefore, it may be possible to omit a reference circuit or to set up compensation circuits without moving parts. Such a system is less susceptible to mechanical trouble. At the same time, the high constancy of power ensures a long operation without recalibration. The luminescent diodes have such a small dimension that coupling of the light into optical waveguides is possible without problems. Thus, the sensitive components can be positioned externally and are not subject to the thermal and mechanical loads of a vapor sterilization.

SUMMARY OF THE INVENTION

Therefore, it is the primary object of the present invention to provide an apparatus for measuring the partial pressure of gases dissolved in liquids, to be used in plants for carrying out biotechnological and food technological processes, by means of optical methods in which the above-described disadvantages of the prior art apparatus is avoided. In particular, the apparatus is to have an increased long-term stability and is to permit a partial gas pressure measurement in a precise manner and in media having a changing chemical-physical composition as well as in media which are clear, turbid or have changing turbidity. The apparatus should have short response times and it should be able to use the apparatus particularly in the case of high partial pressures of the gas.

In accordance with the present invention, the above objects are met by an apparatus including a) a measuring space which is separated by means of a gas-permeable diaphragm which is permeable for the gas to be detected;

b) a light emission source for producing a light ray which penetrates into the measuring space and has a wave length which is absorbed by the gas to be detected;

c) a measuring arrangement for determining the light ray leaving the measuring space; wherein d) the measuring space, the light emission source and the measuring arrangement are arranged in a rod-shaped probe;

e) the probe is capable of being sterilized; and f) the measuring space is filled with a fluid which does not chemically react with the gas to be detected.

Accordingly, in the apparatus according to the present invention, harmful influences of the sample medium, such as discolorations or turbidity, are eliminated by the diaphragm. The gas to be detected diffuses into the diaphragm and is collected in the measuring space. The measuring space can be located entirely within or partially in the diaphragm or also outside of the diaphragm on the side facing away from the sample space. If the measuring space is within the diaphragm, the fluid which does not chemically react with the gas in accordance with feature f) fills out the free spaces of the diaphragm.

In accordance with the invention, there is no chemical reaction taking place between the gas and the fluid present in the measuring space. The gas is merely physically absorbed by the fluid. Consequently, there is no time delay resulting from an intermediate chemical reaction whose sequence additionally would be influenced by numerous other factors and could be impaired as a result.

The fluid present in the measuring space (gas or liquid), which does not chemically react with the gas to be detected, is preferably selected in such a way that it absorbs the gas to be detected well. For this purpose, suitable gases or liquids can be used equally. The type of the mentioned fluid depends on the gas to be measured.

In the field of biotechnology, the fluid should be biologically inert, i.e., compatible. Such suitable fluids are, for example, perfluorochemicals. For example, such chemicals are added to foodstuffs as second liquid phase in order to increase the oxygen introduction into the aqueous phase.

This effect is based on the fact that the perfluorochemicals have a physical absorption capacity for gases which is several times higher than that of water. As substances used in biotechnology, the perfluorochecmicals are per se chemically and biologically inert. A special subgroup of the perfluorchemicals are the perfluorized carbon compounds (also called perfluorocarbons PFC). The carbon structure of these compounds can be freely selected and can be composed, for example, of simple or branched carbohydrates. Also possible are ether and cyclical carbohydrates. Specially preferred are unbranched perfluorized polyethers.

The present invention also is directed to an apparatus of the above-described type which includes a light-conducting element whose border surface is in contact with the measuring space and through which the light of the light emission source is conducted, so that a weakened total reflection occurs at this border surface.

The light-conducting element producing the weakened total reflection will be called ATR (attenuated total reflectance) element in the following. The measuring space synonymously is also referred to as measuring location.

The construction of the ATR element can be selected freely. Included in the possible constructions are the use of prisms, lenses or light wave conductors. They must be capable of absorbing thermal loads when used under vapor sterilization conditions. Particularly quartz glass is available for use in the range UV to NIR. Particularly sapphire is available for light having longer wave lengths. If a light wave conductor is used, quartz glass fibers are suitable for the UV to NIR range, while particularly chalcogenide, fluoride or silver halogenide fibers are suitable for the range with longer wave lengths.

In principle, the diaphragm can be arranged structurally in two different ways relative to the ATR element. If the diaphragm material has no absorption or a constant absorption for the wave length range, the diaphragm can be placed directly on the ATR element. If this is not the case, a gap can be left between the diaphragm and the ATR element, wherein the width of the gap is in the order of magnitude of a few wave lengths of the light.

While in the first case, i.e., diaphragm directly on the ATR element, the measuring location is still within the diaphragm on the side facing the ATR element, in the second case there is a separate space or gap between the ATR element and the diaphragm. In each case, because of the small thickness of the measuring location of only a few micrometers (penetration depth of the totally reflected light) and the immediate vicinity to the diaphragm, the gas to be detected can diffuse from the sample within a very short time into the measuring location. Consequently, partial pressure changes in the sample are registered with an extremely short response time in the range of milliseconds to seconds. In contrast, in an arrangement according to the prior art, the diffusion requires a period in the range of minutes.

Moreover, because of the thin measuring location, the apparatus according to the present invention is particularly suitable for measuring high partial pressures in which, in conventional systems, the absorption of the measuring signal is too great, On the other hand, because of the arrangement of a fluid absorbing the gas between the ATR element and the diaphragm, it is also possible to measure very low partial pressures because the gas collects in this fluid.

The diaphragm is composed of materials which are capable of being sterilized by steam. Diaphragm materials which have been found useful in this field are primarily used. Among these materials are especially silicone, polytetrafluoroethylene as well as other fluorized polymers. For applying the materials onto fibers to form an ATR element, the materials must be capable of being liquified or sprayed, such as particularly polytetrafluoroethylene.

The present invention provides that the measuring space, the light emission source and the measuring arrangement are arranged in a rod-shaped probe. The probe is constructed as an apparatus which can be sterilized if it is used in the field of biotechnology, for example, in fermentations, the production of beverages or waste water purification. Since sterilization is carried out predominantly by means of vapor in the field of fermentation technology, the materials of the probe must be selected accordingly. For this reason, the diaphragm materials which have been found useful in this field are also primarily used in the probe according to the present invention. The materials are especially polytetrafluoroethylene, silicone and other fluoride polymers. In accordance with the present invention, useful gas-selective diaphragms are solubility diaphragms. When inserted in the sample space, these diaphragms are capable of producing an equilibrium between the sample liquid and the internal mixture.

In accordance with a preferred feature of the present invention, luminescent diodes are used as the light emission source. The use of these devices has the following advantages:

The emission has a relatively narrow band width, i.e., the use of interference filters is not absolutely necessary for selectively determining the respective gas. Because of the relatively low current consumption, it is possible in principle to construct the measuring arrangement with battery operation. A decisive advantage as compared to conventional infrared sources is the high constancy of power. Therefore, it may be possible to omit a reference circuit or to set up compensation circuits without moving parts. Such a system is less susceptible to mechanical trouble At the same time, the high constancy of power ensures a long operation without recalibration. The luminescent diodes have such a small dimension that coupling of the light into optical waveguides is possible without problems. Thus, the sensitive components can be positioned externally and are not subject to the thermal and mechanical loads of a vapor sterilization.

In order to increase the accuracy, the method of the present invention can also operate with different wave lengths, preferably two different wave lengths. The methods for increasing the accuracy of the measurements and for compensating the variations in the electronic components are generally known and published (Meas.Sci.Technol. 3(1992)2 191–195, Sean F. Johnston: Gas Monitors Employing Infrared LEDs).

The present invention additionally utilizes detectors which are compatible with the luminescent diodes. Suitable detectors are particularly photodiodes, light-dependent resistors and lead selenide detectors (PbSe-detectors). The latter operate predominantly in the infrared range and are suitable primarily for the determination of carbon dioxide.

Optical waveguides are used for conducting the light waves from the light emission source to the measuring chamber. The same is true for conducting the light from the measuring chamber to the measuring arrangement for determining the non-absorbed light portions. In accordance with the present invention, the measuring arrangement is preferably connected to a special circuit for evaluating, storing and indicating the signals. For this reason, the apparatus according to the present invention is particularly suitable for the automation of plants. By means of an integrated evaluating unit, all data can be automatically collected and supplied to a regulating process.

In accordance with another advantageous feature of the present invention, it is also possible to construct the apparatus so as to be pressure-tight. It is merely necessary to adapt the construction of the housing of the probe accordingly. As a result, the apparatus according to the present invention can be used in pressures of 200 bars. Preferably, the probe is used at pressures of up to 20 bars. When the probe is used for fermentation processes, it is merely necessary to ensure that the probe withstands the increased pressures occurring under sterilization conditions.

The present invention further relates to a method of measuring the partial pressure of gases dissolved in liquids. In this method, the apparatus according to the present invention is emersed in the liquid present in the sample space in such a way that the diaphragm is completely wetted with sample liquid. Consequently, the gas to be determined can selectively diffuse into the measuring space. A light ray is conducted from the light emission source through the measuring chamber by means of optical waveguides. The gas being diffused into the measuring chamber absorbs a portion of the radiation. The non-absorbed portion of the light ray is conducted through an optical waveguide to the measuring arrangement for determining the partial gas pressure. With the aid of the measurement of the non-absorbed light ray, the partial gas pressure can be determined and evaluated by means of appropriate evaluating units, storing units and indicator units.

In accordance with a preferred feature of the invention, an electromagnetic radiation produced by luminescent diodes is used. Particularly preferred is the infrared range.

The apparatus and the method according to the present invention are particularly suitable for use in measuring the partial pressure of carbon dioxide.

Especially the above-described specific problems concerning the measurement of the partial pressure of carbon dioxide are solved. Depending on the measuring range, a gap may be provided which is filled with a carrier fluid. This results in the particular advantages of a short response time and a suitability for determining high partial pressures.

Carbon dioxide represents a significant production factor in the food industry, particularly the beverage industry. In the beverages themselves, carbon dioxide is responsible for the stability thereof and for their refreshing taste. Most determinations are carried out today through simultaneous pressure and temperature measurements.

A measurement of the partial pressure of carbon dioxide is also required for carrying out biotechnical processes in an optimum manner. Of significance in this connection is the fact that the supply of the microorganisms with gases and the inhibiting properties thereof are a function of the respective partial pressures and not of the concentrations. In spite of this recognition, the partial pressure of carbon dioxide is still not sufficiently taken into consideration. A satisfactory solution for determining the partial pressure of carbon dioxide has still not been found up to now. The principle problems in the selection of a suitable determination method were the lack of suitable apparatus and the high chemical stability of the carbon dioxide. Carbon dioxide constitutes the highest oxidation number of carbon and, therefore, is very slow to react at room temperature. Contrary to other heterogenous gases, carbon dioxide in the dissolved form does not produce hydrogen bridge biotechnology. When used in food technology, probes for measuring ranges of up 10 bars can be made available.

When used for the measurement of partial pressures of carbon dioxide in the field of fermentation technology, it is an advantage that a precalibration is possible. This is because a recalibracion cannot be carried out because of the inhibiting influence of carbon dioxide on most organisms. An additional advantage in this field of application is the fact that the probe is capable of being subjected to thermal loads during sterilization and is easily capable of withstanding temperatures of 150° C. Finally, it is an advantage that, contrary to prior art methods using absorption measurement, interferences which also absorb in the infrared range are excluded.

The invention is not limited by the embodiments described above which are presented as examples only but can be modified in various ways within the scope of protection defined by the appended patent claims.

By using the apparatus according to the present invention, especially the aforementioned problems concerning the measurement of partial pressure in carbon dioxide are solved. In this case, the measuring chamber is filled with a carrier fluid for the carbon dioxide. This fluid must have a solubility for carbon dioxide. Another requirement is that the fluid is chemically and biologically inert. For carrying out a vapor sterilization, it is additionally an advantage if the fluid has a higher boiling point than the material being measured, so that pressure variations are essentially avoided. However, in accordance with the present invention, the apparatus is not limited to a certain carrier liquid. Rather, the composition and the chemical nature of the carrier fluid depend on the type of gas to be measured and the conditions under which the probe is used.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

DETAILED DESCRIPTION OF THE PREFERRED EMBODIMENTS

Figure 1:
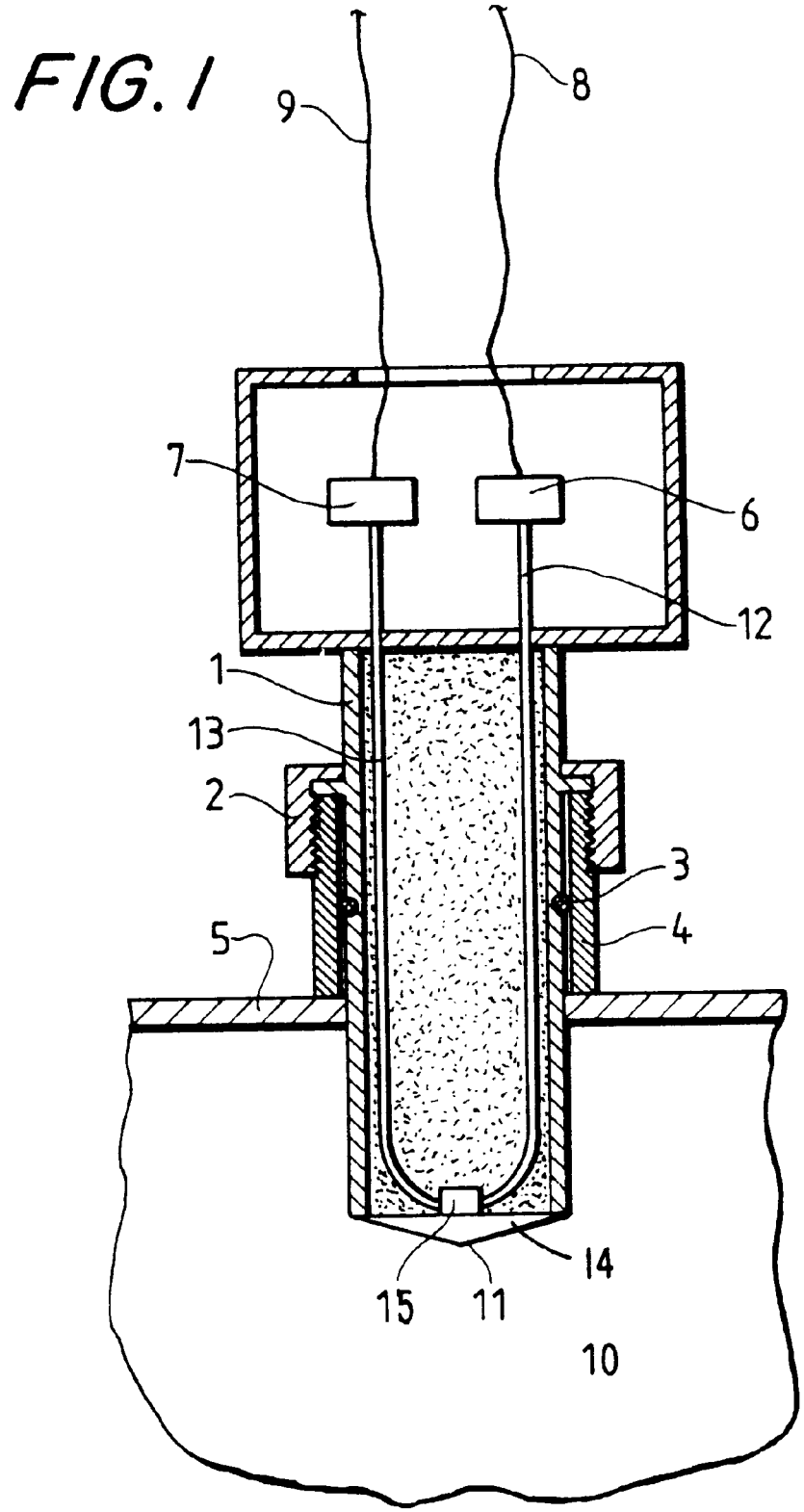
FIG. 1 is a sectional view of the entire probe.

As illustrated in the drawing, the apparatus according to the present invention includes a probe 1. The body of the probe is constructed, for example, of stainless steel. However, the probe may also be constructed of any other suitable material. As a rule, erosion-free materials are used for constructing the probe body.

The probe 1 has a connecting piece 2 which makes it possible to place the probe 1 in a pipe line or in a wall 5 of a vessel in a pressure-tight manner. The connecting piece 2 and an O-ring arrangement 3 make it possible to sealingly fasten the probe 1 in an inlet pipe 4 connected to the wall. 5. The inlet pipe 4 includes a connecting piece corresponding to the connecting piece 2.

This configuration makes it possible to subject the head of the probe to a vapor sterilization and to utilize it in sterile operation.

A light source 6 and a measuring arrangement 7 are provided within the probe 1. In an embodiment of the present invention, the light source 6 is a luminescent diode and the measuring arrangement 7 is a photodetector. Both components are provided with electrical lines 8 and 9. The luminescent diode 6 is supplied with current through line 8. The photodetector 7 transmits a signal pulse through the line 9 to means for amplifying and recording the signal.

The luminescent diode 6 and the photodetector 7 are arranged outside of the liquid space 10. The luminescent diode 6 and the photodetector 7 are connected to extrinsic optical waveguides 12 and 13 which serve to transmit the light from the luminescent diode 6 and the non-absorbed light to the photodetector 7. The optical waveguides may be manufactured of any material suitable for the transmission of light. In the embodiment of the present invention, light in the infrared range is used. Therefore, waveguides preferably of transparent material are used, for example, of silver halides and chalcogenides. These optical waveguides can be subjected to thermal loads and, thus, are suitable for use in an environment which is capable of vapor sterilization.

The ATR element 15 is provided at the end of the head of the probe 1. In the embodiment of the present invention, the ATR element 15 is a sapphire crystal.

The ATR element 15 is separated from the sample space 10 by the gas-permeable diaphragm 11. In the embodiment of the invention, the diaphragm is a thermally stable diaphragm which is made of a material which is capable of being vapor sterilized. In accordance with the invention, polytetrafluoroethelene and/or teflon are preferred as the materials of the diaphragm 11.

The dissolved gas diffuses into the diaphragm 11 into the sample space 10 until an equilibrium is adjusted. The probe 1 determines the partial pressure because the diffusion of gases through a diaphragm is controlled by partial pressure. Consequently, the probe 1 measures a biologically important parameter; this is because, as is the case in all transport processes from the cells or into the cells, the supply of the microorganisms is controlled by partial pressure and by concentration.

The luminescent diode 6 emits a light having a narrow band width which is absorbed selectively by the gas to be determined. In relation to the gas to be determined, the wave length may be in the UV/VIS range as well as in the infrared range. In the case of carbon dioxide, the range is preferably 4.3 $\mu$m. The emitted wavelength range can be limited by a thermal radiator with interference filter or preferably by a luminescent diode having a narrow band width. A particular advantage of the use of the luminescent diode is the fact that the radiation can be modulated, so that the detection is increased and effects such as direct current drift is minimized.

The emitted radiation is conducted through the optical waveguide 12 to the ATR element 15. The existing gas specifically weakens the emitted radiation. The weakened light is partially received by the optical waveguide 13 and is supplied to the photodetector 7. The photodetector 7 measures the weakened light and produces an electrical signal proportional to the weakened light. If modulated light is used, the electrical signal can also be modulated.

An embodiment of the apparatus without ATR element could be produced from the arrangement according to FIG. 1 by removing the ATR element 15. In that case, a chamber filled with fluid (measuring space) would remain behind the diaphragm 11 through which the measuring light could be conducted.

Figure 2:
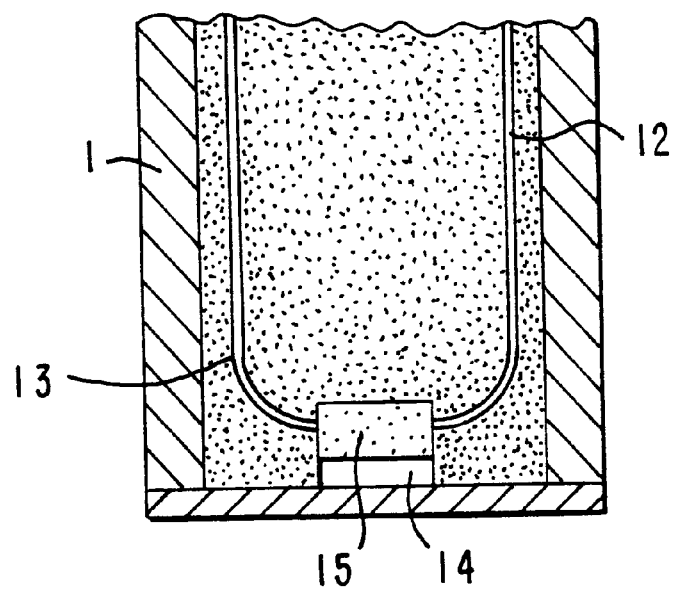
FIG. 2 shows the tip of the probe with gap.

FIG. 2 of the drawing shows the tip of the probe 1 in the situation in which the diaphragm 11 absorbs light at the appropriate wavelength. The ATR element 15 is not arranged flush with the probe head, as is the case in FIG. 1, but somewhat lower, so that a gap 14 results. The gas contained in the sample space 10 now diffuses through the diaphragm 11 into the gap until an equilibrium is reached and the gas can be determined without additional absorption through the diaphragm 11. This same arrangement is selected in the event that low partial pressures are present. In that case, the gap is filled with a carrier fluid which has a high physical absorption capacity for the gas.

This configuration can also be selected when the ATR element 15 is composed of an unsheathed fiber and a gap is used.

Figure 3:
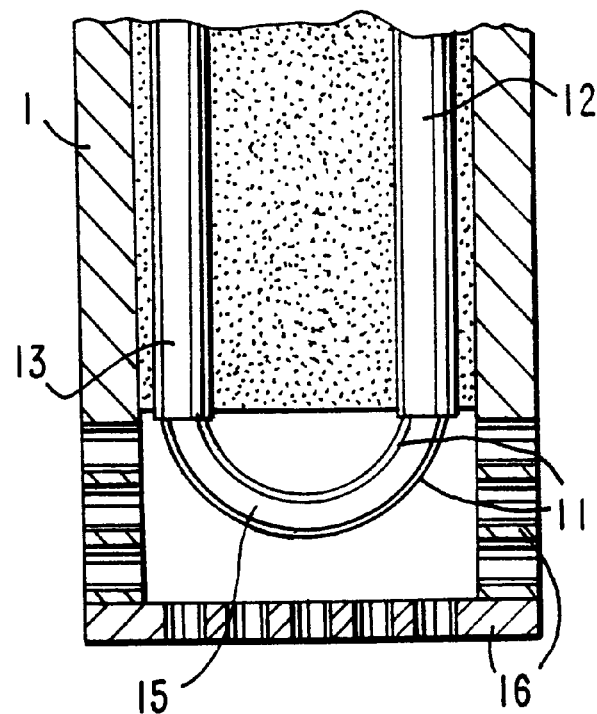
FIG. 3 shows the tip of the probe with light wave conductor as ATR element without gap.

FIG. 3 shows the embodiment of the probe tip in the event that a light-conducting fiber is used as the ATR unit and no gap is lied. The light-conducting fibers 12 and 13 for supplying and removing light, as well as the ATR element 1.5, are of a fiber. The actual ATR element 15 is a light conducting fiber from which the casing has been removed at this stretch. A diaphragm 11 is mounted at this stretch. In order to protect the freely exposed fiber against mechanical loads; from the medium, a cage 16 is fastened to the probe tip.

The advantages achieved by the present invention are particularly that, especially in the case of the measurement of the partial pressure of carbon dioxide, the separation of measuring chamber from sample space prevents influences which would be created by the presence of particles which cause turbidity and which would change in their concentration. In addition, the implementation of the diaphragm ensures the measurement of partial pressure. While it is possible in principle to convert concentration into partial pressures by using Henry's law, this simultaneously requires the knowledge of temperature and pressure and of the media properties. The latter is particularly difficult when used in fermentation media. In addition, the long-term stability, the accuracy and the measuring range are increased as compared to pH-sensitive partial pressure probes.

The particular advantage of the system using an ATR element is the extremely short response time and the suitability for determining high partial pressures. In addition, the construction of the probe is simplified because no separate light radiators and light absorbers must be arranged in which problems with respect to adjustment and sterilization could occur.

The probe according to the present invention can be used especially well in the beverage industry as well as in biotechnology. When used in food technology, probes for measuring ranges of up 10 bars can be made available.

When used for the measurement of partial pressures of carbon dioxide in the field of fermentation technology, it is an advantage that a precalibration is possible. This is because a recalibration cannot be carried out because of the inhibiting influence of carbon dioxide on most organisms. An additional advantage in this field of application is the fact that the probe is capable of being subjected to thermal loads during sterilization and is easily capable of withstanding temperatures of 150° C. Finally, it is an advantage that, contrary to prior art methods using absorption measurement, interferences which also absorb in the infrared range are excluded.

The invention is not limited by the embodiments described above which are presented as examples only but can be modified in various ways Within the scope of protection defined by the appended patent claims.

We claim:

1. An apparatus for measuring a partial pressure of a gas dissolved in a liquid for carrying out biotechnological and food technological processes, the apparatus comprising:

a) a gas-permeable diaphragm configured to separate a measuring space, the gas-permeable diaphragm being permeable for the gas to be detected;

b) a light emission source for producing a light ray directed into the measuring space, wherein the light ray has a wavelength which is absorbed by the gas to be detected;

c) a measuring device for determining the light ray after leaving the measuring space;

d) a rod-shaped probe, wherein the measuring space, the light emission source and the measuring device are mounted in the rod-shaped probe;

e) the probe is capable of being sterilized; and f) the measuring space is filled with a fluid which does not chemically react with the gas to be detected, further comprising g) a solid light-conducting element including a border surface in contact with the measuring space, wherein the light ray produced by the light emission source is conducted through the light-conducting element, such that an attenuated total reflection occurs at the border surface.

2. The apparatus according to claim 1, wherein the probe is capable of being sterilized by steam.

3. The apparatus according to claim 1, wherein the diaphragm is of polytetrafluoroethylene.

4. The apparatus according to claim 1, wherein the diaphragm is a gas-selective solubility diaphragm configured to produce an equilibrium between a sample space and the measuring space.

5. The apparatus according to claim 1, wherein the fluid which does not chemically react with the gas to be determined is perfluorochemical.

6. The apparatus according to claim 1, further comprising an optical waveguide for conducting the light ray from the light emission source to the light conducting element and to the measuring device.

7. The apparatus according to claim 1, wherein the light emission source is luminescent diode.

8. The apparatus according to claim 1, wherein the measuring device comprises one of a photodiode, a light-dependent resistor and a lead selenide photodetector.

9. The apparatus according to claim 1, further comprising a circuit arrangement for evaluating, storing and displaying signals connected to the measuring device.

10. The apparatus according to claim 1, wherein the apparatus is of pressure-tight configuration.

11. The apparatus according to claim 10, wherein the apparatus is configured to operate at pressures of up to 200 bars.

12. The apparatus according to claim 11, wherein the apparatus is configured to operate at pressures of up to 20 bars.

13. The apparatus according to claim 1, wherein the light conducting element is of sapphire.

14. A method of measuring a partial pressure of a gas dissolved in a liquid for carrying out biotechnological and food technological processes, the method comprising separating a measuring space using a gas-permeable diaphragm, wherein the measuring space is filled with a fluid which does not chemically react with the gas to be detected, and wherein the gas-permeable diaphragm is permeable for the gas to be detected, producing a light ray directed into the measuring space by a light emission source, wherein the light ray has a wavelength which is absorbed by the gas to be detected, determining the light ray after leaving the measuring space by a measuring device, wherein the measuring space, the light emission source and the measuring device are mounted in a rod-shaped probe capable of being sterilized, further comprising conducting the light ray produced by the light emission source through a solid light-conducting element including a border surface in contact with the measuring space, such that an attenuated total reflection occurs at the border surface.

15. The method according to claim 14, comprising conducting the light ray through a light-conducting element such that a an attenuated total reflection occurs at border surface between the light conducting element and the measuring space.

16. The method according to claim 14, wherein the measurement is carried out by infrared radiation.

17. The method according to claim 14, comprising conducting the light ray several times to the border surface between the light conducting element and the measuring space for producing an attenuated total reflection at the border surface.

18. The method according to claim 14, comprising determining the partial pressure of oxygen or carbon dioxide.

* * * * *